United States Patent
Von Falkenhausen et al.

(10) Patent No.: US 7,988,997 B2
(45) Date of Patent: Aug. 2, 2011

(54) RAPIDLY-DECOMPOSING ADMINISTRABLE FORM FOR RELEASING ACTIVE INGREDIENTS IN THE ORAL CAVITY OR IN BODILY CAVITIES

(75) Inventors: Christian Von Falkenhausen, Meckenheim (DE); Markus Krumme, Neuwied (DE); Wolfgang Laux, Diez (DE)

(73) Assignee: LTS Lohmann Therapie-Systeme AG, Andernach (DE)

( * ) Notice: Subject to any disclaimer, the term of this patent is extended or adjusted under 35 U.S.C. 154(b) by 927 days.

(21) Appl. No.: 10/332,064

(22) PCT Filed: Jun. 22, 2001

(86) PCT No.: PCT/EP01/07051
§ 371 (c)(1),
(2), (4) Date: Feb. 27, 2003

(87) PCT Pub. No.: WO02/02085
PCT Pub. Date: Jan. 10, 2002

(65) Prior Publication Data
US 2004/0028732 A1  Feb. 12, 2004

(30) Foreign Application Priority Data
Jul. 4, 2000 (DE) .................................. 100 32 456

(51) Int. Cl.
*A61K 9/22* (2006.01)
(52) U.S. Cl. ........................................................ 424/468
(58) Field of Classification Search ............... 424/1, 468
See application file for complete search history.

(56) References Cited

U.S. PATENT DOCUMENTS

| | | | | |
|---|---|---|---|---|
| 4,043,339 | A | * | 8/1977 | Roseman ................. 424/430 |
| 5,135,752 | A | * | 8/1992 | Snipes ..................... 424/435 |
| 5,318,780 | A | * | 6/1994 | Viegas et al. ............. 424/427 |
| 5,503,844 | A | * | 4/1996 | Kwiatek et al. ........... 424/449 |
| 5,529,782 | A | * | 6/1996 | Staab ........................ 424/436 |
| 5,750,585 | A | * | 5/1998 | Park et al. ................. 521/143 |
| 5,783,207 | A | * | 7/1998 | Stanley et al. ............ 424/440 |
| 6,150,424 | A | | 11/2000 | Breitenbach et al. |
| 6,344,222 | B1 | * | 2/2002 | Cherukuri et al. ............ 426/6 |
| 2001/0006677 | A1 | | 7/2001 | Robinson et al. |
| 2002/0028181 | A1 | * | 3/2002 | Miller et al. ............... 424/43 |

FOREIGN PATENT DOCUMENTS

| | | |
|---|---|---|
| DE | 196 35 676 A1 | 3/1998 |
| EP | 0 450 141 A | 10/1991 |
| EP | 0 567 234 A | 10/1993 |
| EP | 0598 606 A | 5/1994 |
| EP | 0 636 378 A | 2/1995 |
| FR | 2 325 389 A | 4/1977 |
| WO | WO 89 06956 A | 8/1989 |
| WO | WO 98 26764 A | 6/1998 |
| WO | WO 00 18365 A | 4/2000 |

* cited by examiner

*Primary Examiner* — Kamal Saeed
*Assistant Examiner* — Kristin Bianchi
(74) *Attorney, Agent, or Firm* — Birch, Stewart, Kolasch & Birch, LLP

(57) ABSTRACT

A dosage form which is, in particular, sheet-like and rapidly disintegrating or soluble in an aqueous environment for rapid release of active ingredients in the oral cavity, in body orifices or in body cavities, where the dosage form comprises a matrix which comprises one or more water-soluble polymers as base substances, and comprises at least one active ingredient, is characterized in that the dosage form is provided with spaces or cavities which are present in the polymeric matrix and whose contents differ in terms of the state of aggregation from the matrix.

54 Claims, No Drawings

RAPIDLY-DECOMPOSING ADMINISTRABLE FORM FOR RELEASING ACTIVE INGREDIENTS IN THE ORAL CAVITY OR IN BODILY CAVITIES

This application is the National Stage under 35 USC §371 of International Application No. PCT/EP01/07051 filed on Jun. 22, 2001, which claims priority under 35 U.S.C. §119 (a)-(d) of Application No. 10032456.8 filed in Germany on Jul. 4, 2000.

The invention relates to preferably shoot-like dosage forms which rapidly disintegrate in an aqueous environment, in particular oral dosage forms, which make possible rapid release of active ingredients in the oral cavity or in other body orifices or body cavities and which have a matrix based on water-soluble polymers as base substances. The invention relates in particular to dosage forms of the type mentioned which are in the form of wafers. The invention also includes processes for the production of such dosage forms.

Pharmaceutical dosage forms, e.g. buccal or sublingual tablets, which release active ingredients in the oral cavity, which are then absorbed through the oral mucosa are advantageous in many respects. They facilitate oral administration of medicaments to certain patients who have difficulty in taking other oral drug forms—e.g. because of problems with swallowing. Since absorption via the oral mucosa avoids passage through the gastrointestinal tract, a rapid onset of action and extensive utilization of active ingredient are ensured. Said advantages also apply to vaginal, rectal and intranasal administration forms.

Suitable oral drug forms which have the aforementioned properties are, beside sublingual or buccal tablets, also sheet-like, wafer-like dosage forms (called wafers). Because their thickness is low and they are capable of rapid disintegration or dissolution they are distinguished in particular by rapid release of medicaments and other active ingredients in the oral cavity. Such wafer-like drug forms are usually composed of film-forming, water-soluble polymers such as, for example, certain cellulose derivatives. On contact with water or saliva, the polymers dissolve and the drug form disintegrates, releasing the active ingredients present therein. The onset and the time course of release of active ingredient depend to a great extent on the thickness of the drug form (of the wafer); the thinner it is, the more rapidly disintegration progresses in an aqueous environment, because the solvent can penetrate faster into the inner regions of the drug form. On the other hand, such drug forms (wafers) must have a certain thickness in order to be able to comply with their intended function, namely to deliver active ingredients. Consequently, the thickness of such dosage forms is essentially determined by the nature and amount of the active ingredient which they contain and are intended to release. As the thickness increases, the disintegration or dissolution of the wafer becomes correspondingly slower. Thicker wafers in particular, but also those with a relatively low thickness, are prone, because of their sheet-like, smooth shape and the retarded disintegration, to stick and become firmly adherent to the roof of the mouth or other surfaces of the oral mucosa. This is caused by the polymer layers dissolving on the surface, which form a tacky and viscid film.

The property of these drug forms of becoming firmly adherent to the roof of the mouth and other surfaces of the oral mucosa may cause an unpleasant sensation for the relevant person or for the patient, i.e. the mouthfeel caused by these wafers is unpleasant or upsetting and therefore in need of improvement.

EP 0 450 141 B2 discloses a carrier material for the administration of drugs which rapidly dissolve on contact with saliva after oral intake. This carrier material has a porous dehydrated skeletal structure and is based, in particular, on proteins and polysaccharides. The cavities produced by dehydration are used for incorporation of liquid active substances. The gelatin/polysaccharide carriers described can also be used in the form of wafers. No measures are provided for reducing the tendency to stick; this risk does exist, however, because the dehydrated carrier materials are rehydrated on contact with saliva at the latest and thus acquire a tacky surface.

It was therefore the object of the present invention to provide a dosage form, in particular an oral dosage form of the aforementioned type, which displays the known advantages of sheet-like, rapidly disintegrating dosage forms and additionally has a reduced tendency to stick or adhere to the oral mucosa and is therefore distinguished by an improved mouthfeel.

The object is achieved according to the invention by providing a dosage form having the features specified in the preamble to claim 1 with spaces or cavities which are present in the polymeric matrix of the dosage form and whose contents differ in terms of the state of aggregation from the matrix. This means in particular that the spaces or cavities comprise gaseous or liquid contents, while the polymer matrix itself has a solid or semisolid state of aggregation. The dosage forms of the invention thus have spatial regions with different phases; said spaces or cavities represent a second phase which may be present in the interior of the polymer matrix (first phase), but it may also extend as far as the outer edge.

On the one hand, the spaces or cavities of the invention facilitate access of water or saliva or other body fluids into the interior of the dosage form (e.g. wafer) and thus speed up the dissolution of the dosage form and the release of active ingredient, which represents an advantage in particular with thicker dosage forms (wafers). On the other hand, the thickness of the walls of said spaces or cavities is low because they represent, for example, solidified bubbles, so that a rapid dissolution or disintegration of these cavities takes place. This alters the internal structure and, as a consequence, also the surface of the dosage form, so that the surface becomes irregular. For example, the surface thus acquires a corrugated structure or irregularities. This and the stiffness of the product prevent the wafer sticking to the oral mucosa.

Because the tendency to stick is reduced, the dosage forms of the invention are distinguished by an improved mouthfeel, which eventually leads to improved acceptance by the users or patients.

The residence time of the dosage forms of the invention at the site of administration (e.g. oral cavity) or the disintegration time is preferably in the range from 1 s to 5 min, more preferably in the range from 5 s to 1 min, and most preferably in the range from 10 s to 30 s.

The invention is not, however, confined to oral dosage forms which release active ingredients in the region of the oral cavity. On the contrary, it also extends to dosage forms which are introduced into other body cavities or body orifices and release their active ingredients there, for example rectal, vaginal or intranasal dosage forms. The released active ingredient is either absorbed at the site of administration, e.g. through the oral mucosa, or it is transported further and absorbed at another site (e.g. in the gastrointestinal tract after the active ingredient released in the oral cavity has been swallowed).

Said spaces or cavities of the dosage form may each be present isolated from one another in the polymeric matrix or preferably in the form of solidified bubbles. Another embodiment provides for said spaces or cavities to be connected to one another, preferably forming a connected channel system penetrating through the matrix.

Suitable dosage forms having the spaces or cavities of the invention are, in particular, polymeric materials which represent solidified foams.

Said spaces or cavities are preferably filled with gas or a gas mixture, in particular air; however, it may also be advantageous for them to contain other gases or gas mixtures. A further embodiment provides for the spaces or cavities to be filled with a liquid or a liquid mixture (for example oils), these liquids not being miscible with the matrix material and not dissolving the polymeric framework. Said liquid or the liquid mixture may additionally comprise one or more active pharmaceutical ingredients.

The total volume of said spaces or cavities, as a proportion of the total volume of the dosage form, is preferably from 5 to 98%, with preference for 50-80%. In this way the intended adhesion-diminishing effect is achieved without impairing too greatly the capacity of the dosage form to take up active ingredient. Another important parameter influencing the properties of the dosage forms of the invention is the diameter of the cavities or bubbles. The bubbles or cavities are preferably produced using a foam-beating machine. It is thus possible to adjust the diameter of the bubbles in a wide range almost as desired. Thus, the diameter of the bubbles or cavities can be in the rang from 0.01 to 50 µm; diameters between 0.1 and 10 µm are particularly preferred.

The cavities of the dosage forms of the invention are preferably free of active ingredient; however, it may be advantageous for these cavities to contain excipients or additives, preferably surfactants or gas-forming substances.

In order to diminish further the tendency of the dosage forms to stick it is possible additionally to make use of the measure of giving the surfaces of the dosage form an uneven or irregular shape, preferably corrugated or like a relief or with a structured surface. Such an irregular surface structure can be caused, for example, by the bubble-like cavities introduced into the polymer matrix and/or by a subsequent special drying treatment.

The matrix of the dosage forms of the invention comprises as base substances a water-soluble polymer or mixtures of such polymers. Preferably used for this purpose are synthetic or partially synthetic polymers or biopolymers of natural origin, which are film-forming and water-soluble and/or which are suitable for foam formation. Particularly suitable polymers are those preferably selected from the group comprising cellulose derivatives, polyvinyl alcohol, polyacrylates and polyvinylpyrrolidone. Particularly preferred cellulose derivatives are hydroxypropylmethylcellulose, carboxymethylcellulose, hydroxypropylcellulose, hydroxymethylcellulose, methylcellulose, and other substituted cellulose derivatives. Likewise preferred are water-soluble polysaccharides of vegetable, microbial or synthetic origin, in particular those polysaccharides which are not cellulose derivatives, such as, for example, pullulan, xanthan, alginates, dextrans, agar-agar, pectins and carrageenan; the last-mentioned is particularly preferred. Also suitable are proteins, preferably gelatin or other gel-forming proteins, and protein hydrolyzates. Suitable protein hydrolyzates include, inter alia, caseinate, whey and vegetable proteins, gelatin and (egg) albumin, and mixtures thereof.

Preferred proteins are caseinates derived from spray-dried dairy products.

The dosage forms of the invention are preferably thin, e.g. in the form of a wafer. The thickness of the dosage form is preferably between 0.1 and 5 mm, particularly preferably between 0.5 and 1 mm. The lower limit for the thickness of the dosage forms is about 50 µm.

Suitable active ingredients are therapeutically active compounds—without restriction. These may be derived from the following groups: agents for treating infections; virostatics; analgesics such as fentanyl, sufentanil, buprenorphine; anesthetics, anorectics; active ingredients for treating arthritis and asthma, such as terbutaline; anticonvulsants; antidepressants; antidiabetics; antihistamines; antidiarrheals; agents for migraine, pruritus, nausea and retching; travel and sea sickness, such as scopolamine and ondansetron; anti-parkinson agents; antipsychotics; antipyretics, spasmolytics, anticholinergics, anti-ulcer agents such as ranitidine, sympathomimetics; calcium channel blockers such as nifedipine; beta blockers; beta agonists such dobutamine; antiarrhythmics; antihypertensives such as atenolol; ACE inhibitors such as nalapril; benzodiazepine agonists such as flumazenil; coronary, peripheral and cerebral vasodilators; stimulants for the central nervous system; hormones; hypnotics; immunosuppressants; muscle-relaxing agents; parasympatholytics; parasympathomimetics; prostaglandins; proteins, peptides; psychostimulants; sedatives; tranquilizers.

Suitable active ingredients for administration in the mouth or onto the oral mucosa are in principle all those able to undergo buccal and/or gastrointestinal absorption. Among these, nicotine is particularly preferred.

The active ingredient content per dose unit is up to 50 mg, preferably up to 30 mg, particularly preferably up to 20 mg.

Further suitable active ingredients are: polishers, abrasives such as titanium dioxide, silicon dioxide etc.; sodium fluoride, dicalcium phosphate; essential oils such as aniseed oil, fennel oil, eucalyptus oil, peppermint oil, spearmint oil, orange oil, sage oil, thyme oil, lemon oil etc.; aromatizers such as camphor, cineol, eucalyptol, menthol, pinene, cinnamaldehyde, cinnamic acid, etc.; honey, citric acid, vitamins, antioxidants, sorbitol. The dosage forms of the invention are thus also suitable for cosmetic applications and for uses in the areas of dental care, tooth cleaning, oral hygiene or dental hygiene.

Further aromatizers which can be added are vanilla flavor, orange flavor, orange zest flavor, strawberry flavor, raspberry flavor or chocolate flavor, each singly or in combination. It is additionally possible to add one or more sweeteners such as sucralose, aspartame, cyclamate, saccharin and acesulfame, and salts thereof.

Suitable excipients are, inter alia, substances from the following group:
carboxymethylcelluose, gum arabic, methylcellulose, pectins, modified and unmodified starches, gelatin, animal and/or vegetable proteins, egg albumin, alginates, Brij (an emulsifier), isopropanol, benzyl alcohol, ethyl acetate, ethyl citrate, octyl gallate, 1,2-propylene glycol, magnesium stearate, stearic acid, microcrystalline cellulose, Aerosil, lecithin, Tween, propyl gallate, amylogam.

It is additionally possible to dissolve a sugar (or a mixture of sugars) or another carbohydrate material in the foam. The sugar or the carbohydrate increases the mass which the foam has after drying. In addition, the drying and the crystallization of the sugar or of another carbohydrate confers on the dried foam an additional strength and stability. The sugar or other carbohydrates may result in the dried foam having a sweet taste or may improve the organoleptic properties of the foam in other ways. Examples of sugars which can be used for this purpose are, inter alia, maltose, lactose, sucrose, dextrose (glucose) and trehalose, and sugar alcohols such as, for example, mannitol, sorbitol, xylitol, maltitol, and the like.

Examples of other suitable carbohydrates are maltodextrin, starch sugar syrup (from corn), soluble starches and the like.

During production of the dosage forms of the invention it is additionally possible to admix one or more acids in order to confer on the foam a pleasant acidic taste. Examples of such acids include, inter alia, citric acid, lactic acid, acetic acid, benzoic acid, propionic acid, oxalic acid, malonic acid, succinic acid, malic acid and tartaric acid. The addition of acid(s) may additionally be necessary or desired in order to reduce the pH of the foam. This is desired in particular when the active ingredient present in the dosage form is relatively insoluble under basic conditions, such as, for example, ibuprofen, or with active ingredients which are unstable under basic conditions.

A further possibility is to add moisturizers or humectants to the dosage forms of the invention, in particular foams, in order to improve the esthetic properties of the dried foam and in order to reduce the fragility or brittleness of the dried foam. Examples of such agents are, inter alia, glycerol, propylene glycol and polyglycerol esters. It is also possible to add, before or after the drying, surface-active substances in order to improve the stability of the foam before or after the drying. Examples of suitable surface-active substances are, inter alia, substituted sorbitan derivatives, in particular those of the Tween series (ICI).

The following processes are proposed for the production of the dosage forms of the invention with improved mouthfeel and reduced tendency to stick.

Firstly a solution or dispersion which comprises at least one water-soluble film-forming polymer and at least one active ingredient is prepared. This solution or dispersion, which may also be a concentrated solution or viscous composition, is subsequently foamed by introducing gas or gas mixture (e.g. air). This can take place by use of a disperser or of a foam-beating machine, but also by other methods, e.g. using ultrasound. Suitable gases are, in particular, also inert gases such as nitrogen, carbon dioxide or helium, or mixtures thereof.

In order to stabilize the foams or compositions containing air bubbles (or containing gas bubbles) which have been produced in this way, a foam-stabilizing agent is added before or during the production of foam. Agents suitable for this purpose, e.g. surfactants, are known to the skilled worker. Finally, the composition containing air bubbles or the foam is spread as film or layer on a suitable substrate and is then dried. Removal of solvent during the drying causes the foam to solidify to an aerogel, during which the cavities which have formed acquire a permanent structure. Wafers with desired surface dimensions or geometric shapes are obtained by pouring the foamed coating composition into appropriate molds or by punching the individual wafers out of a larger-area piece. The active ingredient-containing drug forms obtained in this way have the properties and advantages of the invention. The shape, number and size of the spaces or cavities produced can be influenced by various process parameters, e.g. by the nature and concentration of the polymers, by the viscosity of the polymer composition, by the control of the foaming process, by the selection of the foam-stabilizing agents etc.

Another process of the invention for producing said dosage forms provides, as a modification of the process described above, for a formation of the spaces or cavities in the interior of the polymer matrix to take place by introducing a hydrophobic solvent which is immiscible with the solvent used to prepare said solution or dispersion. In this case, an emulsion which contains the hydrophobic solvent in the form of finely distributed droplets is produced. Removal of the solvents during the subsequent drying leaves droplet- or bubble-shaped cavities behind in the polymer matrix. In the case of a two-phase system, the solvent of the internal phase must be removed first.

A further possibility in a modification of the process described above is to produce said cavities in such a way that excipients which form a gas or gases are added to the polymer- and active ingredient-containing solution or dispersion, whereby the composition is foamed. This foaming through evolution of gas can take place either during the production of the polymer composition or during the coating of this composition onto the substrate, or not until the subsequent drying process. Substances or mixtures of substances suitable for gas formation are known to the skilled worker. The foaming can also be brought about by decompression of a previously dissolved gas. It is possible to use as gas in particular an inert gas such as nitrogen, carbon dioxide or helium, or a mixture thereof.

Production of the dosage forms of the invention may alternatively also start from a melt of the matrix polymer or polymer mixture. The processing is in principle similar to that with hot melt coating compositions known in the prior art.

Gas or a gas mixture is introduced by one of the aforementioned methods into said polymer melt in order to cause foaming of the melt. The melt is then spread or extruded onto a suitable substrate or poured into a mold and then left to cool and solidify. Processing from the melt is unsuitable if the intended active ingredient is unstable or volatile at the melting point of the polymer melt. It is possible if necessary to add excipients to reduce the melting point of the polymer melt. It is also possible in principle to use hot melt coating compositions known from the prior art as long as they meet the conditions stated in claim 1.

In a further modification of the production process described above, the polymer matrix is initially produced in the form of a block. The required sheet-like dosage forms are then removed from the latter by cutting.

The dosage forms of the invention are advantageously suitable for administering medicaments in the oral cavity or for rectal, vaginal or intranasal administration. They can be employed in human medicine and in veterinary medicine.

PRODUCTION EXAMPLE 111.43 g of distilled water are introduced;
22.38 g of Mowiol 8-88* are added with stirring;

* partially hydrolyzed polyvinyl alcohol of low viscosity (supplied by Clariant)

heating of the mixture to 80° C.;
stirring (30 min);
cooling to 40° C.;
addition of 1.8 g of PEG 400,
addition of 1.8 g of PEG 4000;
homogenization;
addition of aspartame (0.18 g) and flavor (5.58 g);
stirring;
addition of 26.46 g of nicotine hydrogen tartrate;
addition of 1.8 g of silicon dioxide;
stirring (2 h) and foam beating at temperature below 50° C.;
spreading;
drying at 60° C. (15 min).
* partially dydrolyzed polyvinyl alcohol of low viscosity (supplied bu Clariant)

The invention claimed is:

1. A dosage form which is sheet-shaped and rapidly disintegrating or soluble in an aqueous environment for rapid release of active ingredients in an oral cavity, in body orifices or in body cavities, where the dosage form comprises a matrix which comprises one or more film forming water-soluble polymers as base substances, and comprises at least one active ingredient, wherein the dosage form is provided with spaces or cavities which are present in the polymeric matrix and whose contents differ in terms of the state of aggregation from the matrix, a thickness of the dosage form is between 0.5 and 1 mm, surfaces of the dosage form have corrugated shapes, and said spaces or cavities are filled with a liquid or a liquid mixture, the liquid(s) being immiscible with the matrix material.

2. The dosage form as claimed in claim 1, wherein the liquid or the liquid mixture comprises one or more active ingredients.

3. A process for the production of the oral dosage form according to claim 1 which is rapidly disintegrating or soluble in an aqueous environment, comprising the following steps:
   a) preparing a solution or dispersion which comprises at least one water-soluble film-forming polymer and at least one active ingredient;
   b) adding a hydrophobic solvent which is immiscible with the solvent used to prepare said solution or dispersion, and preparation of an emulsion which contains the hydrophobic solvent in the form of finely dispersed droplets;
   c) spreading this solution or dispersion on a coating substrate; and
   d) solidifying a film with formation of cavities by drying and removal of the solvent.

4. A process for the production of the oral dosage form according to claim 1 which is rapidly disintegrating or soluble in an aqueous environment, comprising the following steps:
   a) preparing a solution or dispersion which comprises at least one water-soluble film-forming polymer and at least one active ingredient;
   b) adding an excipient or a combination of excipients capable of gas formation;
   c) spreading this solution or dispersion on a coating substrate; and
   d) solidifying a film with formation of cavities by drying and removal of the solvent.

5. A process for the production of the oral dosage form according to claim 1 which is rapidly disintegrating or soluble in an aqueous environment, comprising the following steps:
   a) preparing a polymer-containing melt (hot melt) which comprises at least one water-soluble film-forming polymer and at least one active ingredient;
   b) foaming the melt by decompression of a dissolved gas, where appropriate after previous addition of a foam-stabilizing agent;
   c) spreading the melt on a coating substrate; and
   d) solidifying a film by cooling.

6. A method for administration of active pharmaceutical ingredients to humans or animals, which comprises: applying the dosage form of claim 1 via rectal, vaginal or intranasal administration.

7. A dosage form which is sheet-shaped and rapidly disintegrating or soluble in an aqueous environment for rapid release of active ingredients in an oral cavity, where the dosage form comprises a matrix which comprises one or more film forming, water-soluble polymers as base substances, and comprises at least one active ingredient, wherein the dosage form is provided with spaces or cavities which are present in the polymeric matrix and whose contents differ in terms of the state of aggregation from the matrix, a thickness of the dosage form is between 0.5 and 1 mm, surfaces of the dosage form have corrugated shapes, and said active ingredient is nicotine or nicotine hydrogen tartrate.

8. A process for the production of the oral dosage form according to claim 7, comprising the following steps:
   a) preparing a solution or dispersion which comprises said one or more water-soluble film-forming polymer and nicotine or nicotine hydrogen tartrate;
   b) foaming the solution or dispersion by decompression of a dissolved gas, where appropriate after previous addition of a foam-stabilizing agent;
   c) spreading this solution or dispersion on a coating substrate; and
   d) solidifying a cavity-containing film by drying and removal of the solvent.

9. The process as claimed in claim 3, wherein said active ingredient is nicotine or nicotine hydrogen tartrate.

10. The process as claimed in claim 4, wherein said active ingredient is nicotine or nicotine hydrogen tartrate.

11. The process as claimed in claim 5, wherein said active ingredient is nicotine or nicotine hydrogen tartrate.

12. A method for administration of nicotine or nicotine hydrogen tartrate, which comprises: applying the dosage form of claim 7 in the oral cavity.

13. A dosage form which is sheet-shaped and rapidly disintegrating or soluble in an aqueous environment for rapid release of an active substance, nicotine, in an oral cavity, where the dosage form comprises a matrix which comprises one or more water-soluble, film forming polymers as base substances and the active ingredient nicotine, wherein the dosage form is provided with spaces or cavities which are present in the polymeric matrix and whose contents differ from the matrix in terms of the state of aggregation, said spaces or cavities having a total volume, as a proportion of the total volume of the dosage form, of from 50 to 80%, and said spaces or cavities being present in the matrix isolated from one another or being in the form of bubbles; surfaces of the dosage form have corrugated shapes, and wherein said polymers are selected from the group consisting of cellulose derivatives, polyvinyl alcohol, polyacrylates, polyvinyl pyrrolidone, hydroxypropylmethylcellulose, hydroxymethylcellulose, carboxymethylcellulose, hydroxypropylcellulose, methylcellulose, water-soluble polysaccharides of vegetable or microbial origin, pullulan, xanthan, alginates, dextrans, agar-agar, pectins, carrageenan, proteins, gelatin, caseinates, other gel-forming proteins, and protein hydrolysates.

14. The dosage form as claimed in claim 13, wherein the nicotine is present in the form of a salt nicotine bitartrate.

15. The dosage form as claimed in claim 13, wherein said spaces or cavities are filled with a gas, a gas mixture or air.

16. The dosage form as claimed in claim 13, wherein said spaces or cavities are filled with a liquid or a liquid mixture, the liquid(s) being immiscible with the matrix material.

17. The dosage form as claimed in claim 16, wherein the liquid or the liquid mixture comprises one or more active ingredients.

18. The dosage form as claim in claim 13, wherein said spaces or cavities of the dosage form are free of active ingredient in the state after production.

19. The dosage form as claimed in claim 13, wherein the matrix of the dosage form is a solidified foam.

20. The dosage form as claimed in claim 13, wherein the dosage from is in the form of a wafer, and the thickness of the dosage form is between 50 μm and 5 mm.

21. The dosage form as claimed in claim 13, wherein the matrix and/or said spaces or cavities comprise excipients, additives, surfactants, gas-forming substances, moisturizers, humectants or substances that improve the stability of foam.

22. A process for the production of the oral dosage form according to claim 13 which is rapidly disintegrating or soluble in an aqueous environment, comprising the following steps:
 a) preparing a solution or dispersion which comprises said one or more water-soluble film-forming polymer and the active ingredient nicotine;
 b) foaming the solution or dispersion by chemical production of gas or by decompression of a dissolved gas, where appropriate after previous addition of a foam-stabilizing agent;
 c) spreading this solution or dispersion on a coating substrate; and
 d) solidifying a cavity-containing film by drying and removal of the solvent.

23. A process for the production of the oral dosage form according to claim 13 which is rapidly disintegrating or soluble in an aqueous environment, comprising the following steps:
 a) preparing a solution or dispersion which comprises at least one water-soluble film-forming polymer and the active ingredient nicotine;
 b) adding a hydrophobic solvent which is immiscible with the solvent used to prepare said solution or dispersion, and preparation of an emulsion which contains the hydrophobic solvent in the form of finely dispersed droplets;
 c) spreading this solution or dispersion on a coating substrate; and
 d) solidifying a film with formation of cavities by drying and removal of the solvent.

24. A process for the production of the oral dosage form according to claim 13 which is rapidly disintegrating or soluble in an aqueous environment, comprising the following steps:
 a) preparing a solution or dispersion which comprises at least one water-soluble film-forming polymer and the active ingredient nicotine;
 b) adding an excipient or a combination of excipients capable of gas formation;
 c) spreading this solution or dispersion on a coating substrate; and
 d) solidifying a film with formation of cavities by drying and removal of the solvent.

25. A process for the production of the oral dosage form according to claim 13 which is rapidly disintegrating or soluble in an aqueous environment, comprising the following steps:
 a) preparing a polymer-containing melt (hot melt) which comprises at least one water-soluble film-forming polymer and the active ingredient nicotine;
 b) foaming the melt by introducing gas or gas mixture or by chemical production of gas or by decompression of a dissolved gas, where appropriate after previous addition of a foam-stabilizing agent;
 c) spreading the melt on a coating substrate; and
 d) solidifying a film by cooling.

26. The process as claimed in claim 22, wherein steps c) and d) are replaced or modified by following steps c) and d):
 c) producing the polymer matrix in a form of a block, starting from the solution or dispersion or from a melt; and
 d) cutting the solidified block in order to obtain sheet-shaped forms.

27. The process according to claim 22, wherein nicotine is added as the salt nicotine bitartrate.

28. A method for administration of active pharmaceutical ingredients, which comprises:
 applying the dosage form of claim 13 in an oral cavity.

29. A method for administration of active pharmaceutical ingredients to humans or animals, which comprises:
 applying the dosage form of claim 13 via rectal, vaginal or intranasal administration.

30. A dosage form which is sheet-shaped and rapidly disintegrating or soluble in an aqueous environment for rapid release of active ingredients in an oral cavity, where the dosage form comprises a matrix which comprises one or more film forming, water-soluble polymers as base substances, and comprises at least one active ingredient, wherein
 the matrix of the dosage form is a solidified foam,
 said polymers comprise a mixture of polyvinyl alcohol and polyethylene glycol,
 the dosage form is provided with spaces or cavities which are present in the polymeric matrix and whose contents differ in terms of the state of aggregation from the matrix, said matrix being solid and said contents being gaseous;
 a thickness of the dosage form is between 0.5 and 1 mm,
 surfaces of the dosage form have corrugated shapes, and
 said active ingredient is nicotine or nicotine hydrogen tartrate.

31. The dosage form as claimed in claim 30, wherein said matrix further contains silicon dioxide.

32. A dosage form which is sheet-shaped and rapidly disintegrating or soluble in an aqueous environment for rapid release of an active substance nicotine in an oral cavity, where the dosage form comprises a matrix which is a solidified foam and which comprises one or more water-soluble, film-forming polymers as base substances and the active ingredient nicotine, wherein
 the dosage form is provided with spaces or cavities which are present in the polymeric matrix and whose contents differ from the matrix in terms of the state of aggregation, said matrix being solid and said contents being gaseous;
 surfaces of the dosage form have corrugated shapes,
 wherein said polymers are selected from the group consisting of cellulose derivatives, polyacrylates, polyvinyl pyrrolidone, hydroxypropylmethylcellulose, hydroxymethylcellulose, carboxymethylcellulose, hydroxypropylcellulose, methyl-cellulose, water-soluble polysaccharides of vegetable or microbial origin, pullulan, xanthan, alginates, dextrans, agar-agar, pectins, carrageenan, proteins, gelatin, caseinates, other gel-forming proteins, and protein hydrolsates, and
 wherein said matrix further comprises polyethylene glycol which is present in admixture with polyvinyl alcohol.

33. The dosage form as claimed in claim 32, wherein said matrix further contains silicon dioxide.

34. The dosage form as claimed in claim 13, wherein said polymers are selected from the groups consisting of polyacrylates, polyvinyl pyrrolidone, proteins, gelatin, caseinates, other gel-forming proteins, and protein hydrolysates.

35. The dosage form as claimed in claim 7, wherein said spaces or cavities are free of active ingredient.

36. The dosage form as claimed in claim 32, wherein said spaces or cavities are free of active ingredient.

37. The dosage form as claimed in claim 7, wherein said spaces or cavities contain excipients or additives.

38. The dosage form as claimed in claim 13, wherein said spaces or cavities contain excipients or additives.

39. A dosage form which is sheet-shaped and rapidly disintegrating or soluble in an aqueous environment for rapid release of active ingredients in an oral cavity, where the dosage form comprises a matrix which comprises one or more film forming, water-soluble polymers as base substances, and comprises at least one active ingredient, wherein the dosage form is provided with spaces or cavities which are present in the polymeric matrix and whose contents differ in terms of the state of aggregation from the matrix, a thickness of the dosage form is between 0.5 and 1 mm, surfaces of the dosage form have corrugated shapes, said active ingredient is nicotine or nicotine hydrogen tartrate, and wherein the dosage form has spatial regions with different phases.

40. The dosage form of claim 39, wherein the spaces or cavities present in the polymeric matrix are filled with a gas or a liquid immiscible with the matrix material.

41. The dosage form of claim 39, wherein the total volume of spaces or cavities, as a proportion of the total volume of the dosage form, is from 5 to 98%.

42. The dosage form of claim 39, wherein the total volume of spaces or cavities, as a proportion of the total volume of the dosage form, is from 50-80%.

43. The dosage form as claimed in claim 30, wherein said spaces or cavities have a total volume, as a proportion of the total volume of the dosage form, of from 50 to 80%.

44. The dosage form as claimed in claim 32, wherein said spaces or cavities have a total volume, as a proportion of the total volume of the dosage form, of from 50 to 80%.

45. The dosage form as claimed in claim 7, wherein said spaces or cavities have a total volume, as a proportion of the total volume of the dosage form, of from 50 to 80%.

46. The dosage form as claimed in claim 7, wherein said water-soluble polymers are selected from the group consisting of pullulan, xanthan, alginates, dextrans, agar-agar, pectins and carrageenan.

47. The dosage form as claimed in claim 7, wherein said water-soluble polymers are selected from the group consisting of proteins and protein hydrolysates.

48. The dosage form as claimed in claim 7, wherein said water-soluble polymers comprise caseinates.

49. The dosage form as claimed in claim 7, wherein said water-soluble polymers comprise polyethylene glycol 400 and polyethylene glycol 4000.

50. The dosage form as claimed in claim 13, wherein said water-soluble polymers are selected from the group consisting of pullulan, xanthan, alginates, dextrans, agar-agar, pectins and carrageenan.

51. The dosage form as claimed in claim 13, wherein said water-soluble polymers are selected from the group consisting of proteins and protein hydrolysates.

52. The dosage form as claimed in claim 13, wherein said water soluble polymers comprise caseinates.

53. The dosage form as claimed in claim 13, wherein said water soluble polymers comprise polyethylene glycol 400 and polyethylene glycol 4000.

54. The dosage form as claimed in claim 30, wherein said polyethylene glycol comprises polyethylene glycol 400 and polyethylene glycol 4000.

* * * * *